(12) United States Patent
Jones et al.

(10) Patent No.: US 9,120,733 B2
(45) Date of Patent: Sep. 1, 2015

(54) DISTILLATION METHOD FOR THE PURIFICATION OF SEVOFLURANE AND THE MAINTENANCE OF CERTAIN EQUIPMENT THAT MAY BE USED IN THE DISTILLATION PROCESS

(71) Applicant: HALOCARBON PRODUCTS CORPORATION, North Augusta, SC (US)

(72) Inventors: Barry Jones, Augusta, GA (US); Joel Swinson, Augusta, GA (US); Paul Mazzell, Augusta, GA (US)

(73) Assignee: HALOCARBON PRODUCTS CORPORATION, North Augusta, SC (US)

( * ) Notice: Subject to any disclaimer, the term of this patent is extended or adjusted under 35 U.S.C. 154(b) by 0 days.

(21) Appl. No.: 13/683,934

(22) Filed: Nov. 21, 2012

(65) Prior Publication Data

US 2013/0081935 A1 Apr. 4, 2013

Related U.S. Application Data

(60) Continuation of application No. 12/833,676, filed on Jul. 9, 2010, now abandoned, which is a division of application No. 12/113,655, filed on May 1, 2008, now abandoned.

(51) Int. Cl.
*C07C 41/42* (2006.01)
(52) U.S. Cl.
CPC ..................... *C07C 41/42* (2013.01)
(58) Field of Classification Search
USPC ........................................................ 568/683
See application file for complete search history.

(56) References Cited

U.S. PATENT DOCUMENTS

| | | | |
|---|---|---|---|
| 2,921,858 A | 1/1960 | Hall | |
| 2,992,276 A | 7/1961 | Weinmayr | |
| 3,667,487 A | 6/1972 | Schoenbeck et al. | |
| 4,250,334 A | 2/1981 | Coon et al. | |
| 4,432,808 A * | 2/1984 | Heubusch | 134/3 |
| 4,613,405 A | 9/1986 | Godbille | |
| 4,657,638 A * | 4/1987 | le Grand et al. | 202/158 |
| 5,684,211 A | 11/1997 | Kawai et al. | |
| 5,811,596 A * | 9/1998 | Kawai et al. | 568/683 |
| 5,969,193 A * | 10/1999 | Terrell | 568/683 |
| 5,990,176 A | 11/1999 | Bieniarz et al. | |
| 6,074,668 A | 6/2000 | Flament-Garcia et al. | |
| 6,083,514 A | 7/2000 | Chang | |
| 6,162,443 A | 12/2000 | Flament-Garcia et al. | |
| 6,288,127 B1 | 9/2001 | Bieniarz et al. | |
| 6,444,859 B2 | 9/2002 | Bieniarz et al. | |
| 6,469,219 B1 | 10/2002 | Khrimian et al. | |
| 6,558,679 B2 | 5/2003 | Flament-Garcia et al. | |
| 6,677,492 B2 | 1/2004 | Bieniarz et al. | |
| 7,816,409 B2 | 10/2010 | Pacheco et al. | |
| 2003/0200963 A1 | 10/2003 | Flament-Garcia et al. | |
| 2004/0048932 A1 | 3/2004 | Bieniarz et al. | |
| 2005/0113603 A1 * | 5/2005 | Belmonte et al. | 562/408 |
| 2006/0258755 A1 * | 11/2006 | Terrell et al. | 514/715 |

FOREIGN PATENT DOCUMENTS

WO 9725303 7/1997

* cited by examiner

*Primary Examiner* — Rosalynd Keys
(74) *Attorney, Agent, or Firm* — Norris McLaughlin & Marcus, P.A.

(57) ABSTRACT

Processes for preparing commercial quantities of a stable, pharmaceutically acceptable sevoflurane substantially free of impurities are claimed. In another embodiment, a process for removing reactive metal salts from the surface of metallic equipment used in the distillation of sevoflurane and rendering a non-inert metallic surface of the metallic equipment inert.

24 Claims, No Drawings

DISTILLATION METHOD FOR THE PURIFICATION OF SEVOFLURANE AND THE MAINTENANCE OF CERTAIN EQUIPMENT THAT MAY BE USED IN THE DISTILLATION PROCESS

This application is a continuation of U.S. patent application Ser. No. 12/833,676, filed Jul. 9, 2010, which is a divisional of U.S. patent application Ser. No. 12/113,655, filed May 1, 2008, which is incorporated herein by reference.

BACKGROUND OF THE INVENTION

Sevoflurane is produced by several known methods. A commonly used method involves the reaction of formaldehyde (or a formaldehyde equivalent), hydrogen fluoride (HF), and hexafluoroisopropanol (HFIP). U.S. Pat. No. 4,250,334 describes a process in which HFIP is added to a mixture of a stoichiometric excess of paraformaldehyde and HF plus sufficient sulfuric acid to sequester most of the water formed in the reaction. WO 97/25303 describes a process for the production of sevoflurane in which essentially pure bis(fluoromethyl)ether (BFME) is allowed to react with HFIP and sulfuric acid. U.S. Pat. No. 6,469,219 describes a process in which HFIP and a formaldehyde equivalent are allowed to react with excess HF under distillative or extractive conditions in order to produce sevoflurane. Other synthetic routes generate a different impurity profile, but still require a final distillation in order to produce a pharmaceutically acceptable form of sevoflurane.

In all of these processes, unreacted HFIP may remain in the product mixture, as well as BFME, methyl hexafluoroisopropyl ether (MHFIP), polyethers containing the HFIP and formaldehyde moieties, and various other undesired species. These impurities must be removed from the crude sevoflurane product in order to obtain a pharmaceutically acceptable form of the material.

Many of these impurities can be removed by distillation, but it has been disclosed in U.S. Pat. No. 5,684,211 that crude sevoflurane can decompose or disproportionate under distillative conditions and that the product could not be adequately purified as a result of this decomposition/disproportionation. For example, dehydrofluorination of sevoflurane may occur during distillation, leading to fluoromethyl 1,1,3,3,3-pentafluoroisopropenyl ether (also known as Compound A) as a new impurity. It is difficult to separate this decomposition/disproportionation product from sevoflurane by distillation because their boiling points are very similar.

This type of decomposition can be prevented by the use of a decomposition suppressive agent in the distillation process. Suppressive agents known in the art include hydroxides of alkali metals, hydrogenphosphates of alkali metals, phosphates of alkali metals, hydrogencarbonates of alkali metals, borates of alkali metals, sulfites of alkali metals, alkali metal salts of acetic acid, alkali metal salts of phthalic acid and boric acid. Potential drawbacks to the use of such agents, however, include added expense for their use and disposal, as well as the necessity to completely remove them from the drug product.

Furthermore, although fluoroethers are excellent anesthetic agents, some fluoroethers have been reported to encounter stability problems. More specifically, it has been reported (U.S. Pat. No. 5,990,176 and others) that certain fluoroethers, in the presence of one or more Lewis acids, degrade into several by-products including potentially toxic chemicals such as HF and/or HFIP. Hydrofluoric acid is toxic by ingestion and inhalation and is highly corrosive to skin and mucous membranes. Therefore, the degradation of fluoroethers to chemicals such as HF is of great concern to the medical community. In fact, quantities of Ultane® brand sevoflurane had to be recalled on two occasions due to potentially patient-threatening decomposition caused by exposure to Lewis acids.

The Lewis-acid induced decomposition of sevoflurane can be suppressed by the addition of certain Lewis-acid inhibitors to the product. Lewis-acid inhibitors include, but are not limited to, water, butylated hydroxytoluene, methylparaben, propofol, thymol, and propylparaben. The drawbacks of using such agents include the added expense and processing time for their incorporation into the drug product.

Thus, a distillative method is needed for the efficient separation of sevoflurane from impurities without further decomposition/disproportionation that does not require the use of any type of suppressive agent in order to achieve a substantially pure product. Also, this method should result in a product that does not decompose over long periods of time, thus eliminating the need for the addition of sevoflurane decomposition suppression agents.

SUMMARY OF THE INVENTION

The present invention relates to a process for obtaining commercial quantities of substantially pure fluoromethyl 1,1,1,3,3,3-hexafluoroisopropyl ether (sevoflurane) without decomposition-causing impurities or decomposition-suppression agents. The process includes providing a crude sevoflurane product, fractionally distilling the crude sevoflurane product, forming thereby a distillate, and removing substantially pure sevoflurane from the distillate. The distillation takes place in equipment having common distillation components. The surfaces of the components that contact sevoflurane contain little or no active metal salts during the time the surface contacts the sevoflurane. The resulting substantially pure sevoflurane is stable when stored at room temperature for at least two years. There is no requirement for the presence of sevoflurane decomposition suppression agents during storage, and the substantially pure sevoflurane is preferably stored in the absence of such suppression agents.

A commercial quantity of sevoflurane is an amount more than about 500 liters per year, preferably more than about 1000 liters per year, and most preferably more than about 2000 liters per year.

Substantially pure sevoflurane is sevoflurane which contains less than 300 ppm of total impurities, and less than 100 ppm of any individual impurity. In a preferred embodiment, the "substantially pure sevoflurane" contains less than 100 ppm of total impurities, and less than 20 ppm of any individual impurity.

Since the sevoflurane of the present invention is substantially free of impurities that may lead to decomposition, there is no need for special containers to store the sevoflurane. Therefore, the sevoflurane may be stored in common glass for up to two years and even longer, e.g., three, four, or five years. The preferred glass is Type III glass.

In a preferred embodiment, the distillation is conducted in the absence of sevoflurane decomposition suppression agents. In another preferred embodiment, sevoflurane decomposition suppression agents are not added to the substantially pure sevoflurane product subsequent to distillation, e.g., during storage.

Some examples of sevoflurane decomposition suppression agents include hydroxides of alkali metals, hydrogenphosphates of alkali metals, phosphates of alkali metals, hydrogencarbonates of alkali metals, borates of alkali metals, sulfites of alkali metals, alkali metal salts of acetic acid, alkali metal salts of phthalic acid and boric acid. Some additional examples of sevoflurane decomposition suppression agents include Lewis-acid inhibitors. Lewis-acid inhibitors include, but are not limited to, butylated hydroxytoluene, methylparaben, propofol, thymol, and propylparaben.

It should be noted that water is a Lewis-acid inhibitor. Nevertheless, in this embodiment, water may be present in substantially pure sevoflurane, usually as a result of previous processing. In a preferred embodiment, however, water is not added during the distillation process or during storage, and the substantially pure sevoflurane product does not use ambient or remaining water (nor does it serve) as a Lewis acid inhibitor. The resulting sevoflurane preferably contains less than 100 ppm of water, and, in a preferred embodiment, contains less than 70 ppm of water.

The common distillation components include, for example, reboilers, condensers, fractionating columns, transfer lines, and/or storage vessels. The fractionating column preferably contains one or more materials that aid fractionation. Such materials include, for example, column packing materials, plates, sieve trays, or bubble cap trays. In a preferred embodiment, the column packing materials include PFA. The components may also include an agitator.

In one embodiment, the surface of at least one component is metallic. The metallic surface may be made of any metal that can be fashioned into distillation equipment and does not easily form salts. The metallic component should also be stable when in contact with vapor or liquid phases of a crude sevoflurane product or of substantially purified sevoflurane. The metallic surfaces include, for example, stainless steel, a nickel-copper alloy, alloy 20, copper, nickel, zirconium, titanium, tantalum, chromium, Hastelloys or generic equivalents, or combinations thereof. For example, Hastelloy C-276 is sold generically as Alloy C-276, and Hastelloy C-22 is sold generically as Alloy C-22. In a preferred embodiment, the metal is stainless steel, and more preferably the stainless steel is type 316. An example of a nickel-copper alloy is Monel or its generic equivalents. Monel 400 is the preferred Monel.

In another embodiment, the surface of at least one component is non-metallic. The non-metallic surface may be made of any non-metal that can be fashioned into distillation equipment and is stable when in contact with vapor or liquid phases of a crude sevoflurane product or of substantially purified sevoflurane. Some examples of non-metallic surfaces include plastics, glass, carbon, ceramic, and combinations thereof. Preferable plastics include fluorinated polymers, polyethylene, polypropylene, or combinations thereof. Preferable fluorinated polymers include poly(tetrafluoroethylene) (PTFE), fluorinated ethylene propylene (FEP), perfluoroalkoxy polytetrafluoroethylene (PFA), ethylene tetrafluoroethylene (ETFE), polyvinylidene fluoride (PVF), ethylene chlorotrifluoroethylene (ECTFE), polyvinylidene difluoride (PVDF), polychlorotrifluoroethylene (PCTFE), and combinations thereof. In a preferred embodiment, the surface is PFA.

Another aspect of the invention relates to a process as described above, wherein the crude sevoflurane product is provided by reacting a composition comprising hexafluoroisopropanol, formaldehyde or its equivalent, and hydrogen fluoride (HF). The crude sevoflurane product contains hexafluoroisopropanol, and may contain unreacted starting materials, such as HF.

In a preferred embodiment, the amount of HF in the crude sevoflurane is reduced prior to distillation. The amount of HF may be reduced in accordance with known procedures, such as those described in U.S. Pat. No. 6,469,219, Examples 4-6.

Another aspect of the invention relates to a process for removing reactive metal salts from the surface of metallic equipment used in the distillation of sevoflurane and rendering a non-inert surface of the metallic equipment inert (i.e., inerting). The surface of the metallic equipment is any surface of the equipment that may come in contact with vapor or liquid phases of a crude sevoflurane product or of substantially purified sevoflurane during the distillation.

Inerting, e.g., passivating, may be accomplished by methods that are well known in the art. Such methods include, for example, chemical and electrical treatments. Some examples of chemical treatments include phosphate treatments, for example Parkerizing, as well as oxalate and chromium treatments. Some additional inerting methods include galvanizing and painting. Anodizing is particularly useful in the case of aluminum.

The process of the invention includes i) washing the interior surfaces of the metallic equipment one or more times with water. If the pH of the discharged wash is initially less than 6, washing is carried out until the pH of the discharged water is at least 6. Subsequent steps include ii) contacting interior surfaces of the equipment with an aqueous solution of a passivation agent; iii) removing the aqueous passivation solution; and iv) rinsing the equipment with water until the pH of the discharged water is not less than 6. The interior surfaces of the equipment may be contacted with an aqueous solution of a passivation agent by immersing the surfaces in an aqueous solution of a passivation agent or by spraying an aqueous solution of a passivation agent onto the surfaces.

In this specification, an "interior surface," "sevoflurane-contacting surface," or a "liquid- and gas-contacting surface" is a surface of distillation equipment that contacts crude or substantially purified sevoflurane in either the gas or liquid phase during the distillation process.

A passivation agent is any agent that renders the non-inert surface of a metal, especially stainless steel, inert. Some examples of passivation agents include citric acid, nitric acid, and a mixture of nitric acid and sodium or potassium dichromate. A commercial example of a citric acid passivation agent is the CitriSurf product line supplied by Stellar Solutions, 4511 Prime Parkway, McHenry, Ill. 60050. The preferred passivation agent is nitric acid. Preferred mole percent ratios of nitric acid and sodium or potassium dichromate in mixtures of the two include 5:95 to 95:5.

In one embodiment, the concentration of the passivation agent is preferably a minimum of about 1% by weight of the aqueous solution, and more preferably a minimum of about 10% by weight of the aqueous solution. In another embodiment, the concentration of the passivation agent is a maximum of about 90% by weight of the aqueous solution, more preferably a maximum of about 50% by weight of the aqueous solution.

The metallic equipment is preferably in contact with the aqueous passivation solution for a minimum total time period of about 0.25 hours, and more preferably a minimum total time period of about 0.5 hour. The metallic equipment is preferably in contact with the aqueous solution for a maximum total time period of about 48 hours, and more preferably a maximum total time period of about 24 hours.

The contact temperature when the metallic equipment is in contact with the aqueous passivation solution is a minimum of about 20° C., more preferably a minimum of about 35° C., and more preferably about a minimum of about 50° C. The contact temperature when the metallic equipment is in contact with the aqueous passivation solution is a maximum of about 80° C., preferably a maximum of about 70° C., and more preferably about a maximum of about 60° C. The preferred range is about 50° C. to about 60° C.

In another embodiment, the invention relates to a process for obtaining commercial quantities of substantially pure sevoflurane. The process includes i) providing a crude sevoflurane product; ii) passivating liquid- and gas-contacting surfaces of distillation equipment capable of providing commercial quantities of sevoflurane; iii) distilling the crude sevoflurane product in the distillation equipment; and iv) recovering substantially pure sevoflurane. The passivating and distilling steps are described above in further detail.

DETAILED DESCRIPTION

The present invention provides an improved process for preparing commercial quantities of stable, pharmaceutically acceptable sevoflurane substantially free of impurities and without the use of decomposition suppression agents.

The phrase "substantially pure sevoflurane," as used herein is sevoflurane which contains less than 300 ppm of total impurities, and less than 100 ppm of any individual impurity. In a preferred embodiment, the term "substantially pure sevoflurane" means sevoflurane which contains less than 100 ppm of total impurities, and most preferably less than 20 ppm of any individual impurity. Total impurities are defined as impurities not including water.

The term "stable" as used herein means that the substantially pure sevoflurane remains substantially pure as herein defined for at least two years from the time of production at ambient temperature, or for at least three months at 40° C. Stability is achieved without the addition of sevoflurane decomposition suppression agents. Some examples of sevoflurane decomposition suppression agents include hydroxides of alkali metals, hydrogenphosphates of alkali metals, phosphates of alkali metals, hydrogencarbonates of alkali metals, borates of alkali metals, sulfites of alkali metals, alkali metal salts of acetic acid, alkali metal salts of phthalic acid and boric acid. Some additional examples of sevoflurane decomposition suppression agents include, but are not limited to, Lewis-acid inhibitors. Lewis-acid inhibitors include, but are not limited to, butylated hydroxytoluene, methylparaben, propofol, thymol, and propylparaben. It should be noted that water also is a Lewis-acid inhibitor. Nevertheless, in this embodiment, water may be present, usually as a result of previous processing. In a preferred embodiment, water is not added to any water than may already be present during the distillation process.

A commercial quantity of sevoflurane is an amount more than about 500 liters per year, preferably more than about 1000 liters per year, and most preferably more than about 2000 liters per year.

A crude sevoflurane product comprising unacceptably high levels of impurities can be purified by distilling the crude sevoflurane product using process equipment that contains little or no active metal salts. Such surfaces do not contain enough active metal salts to cause significant decomposition/disproportionation of the product. Purified sevoflurane distilled from this type of equipment is stable, without the addition of sevoflurane decomposition suppression agents, for at least two years when stored at ambient temperature and/or for at least three months at 40° C. It should be noted that water may be present as a result of previous processing, but is not added.

The crude sevoflurane product can be prepared in any manner. Preferably the crude sevoflurane product is produced by a process comprising reacting hexafluoroisopropanol (HFIP), formaldehyde, and hydrogen fluoride (HF). Preferably, the reaction is carried out in a stoichiometric excess of HF. The reaction temperature is not critical, but the yields are substantially improved above 50° C. Preferably, the reaction is conducted under autogenous pressure of 30-40 psig ensuring temperatures of 45-75° C. The process is described in U.S. Pat. No. 6,469,219, which is hereby incorporated by reference.

In a preferred embodiment, the amount of HF in the crude sevoflurane is reduced prior to distillation. The amount of HF is reduced in accordance with known procedures such as those described in U.S. Pat. No. 6,469,219, Examples 4-6 to obtain a second crude sevoflurane product.

The term "formaldehyde" as used herein means not only formaldehyde per se, but also any equivalent of formaldehyde. Equivalents of formaldehyde include formaldehyde polymers, such as trioxane, and paraformaldehyde.

Fractional distillation is a widely used, well-understood commercial process. The equipment used in such a process includes, but is not limited to, reboilers, condensers, fractionating column, transfer lines, and storage vessels. A fractionating column may include column packing materials, plates, sieve trays, and bubble cap trays. The equipment may further comprise agitators, transfer lines, packing and packing support hardware, nuts and bolts, pipe fittings and components such as tees, elbows, and valves, and instrumentation such as that used for measuring differential pressure, absolute pressure, and temperature.

The appropriate selection of materials for construction of surfaces of the equipment depends on well-established factors such as temperature stability, compatibility with chemical compounds, cost, etc. In particular, compatibility with sevoflurane and resistance to acidity/basicity should be considered.

Appropriate non-metallic materials for construction of surfaces of the equipment include, but are not limited to, plastics such as fluorinated polymers and polyolefins; glass; carbon; ceramics; and combinations thereof. Examples of fluorinated polymers include, but are not limited to, poly(tetrafluoroethylene) (PTFE), fluorinated ethylene propylene (FEP), perfluoroalkoxy polytetrafluoroethylene (PFA), ethylene tetrafluoroethylene (ETFE), polyvinylidene fluoride (PVF), ethylene chlorotrifluoroethylene (ECTFE), polyvinylidene difluoride (PVDF), polychlorotrifluoroethylene (PCTFE). Fluorinated polymers sold by DuPont under the tradename TEFLON® and their generic equivalents are particularly useful in this invention. Examples of polyolefins include, but are not limited to, polyethylene and polypropylene.

Appropriate metals for the construction of equipment involved in the fractional distillation of sevoflurane include any metal typically used in making distillation equipment. Metals appropriate for making the distillation equipment of the invention do not easily form salts. Examples of appropriate metals include, but are not limited to, higher grades of stainless steel (such as 316 stainless steel), nickel-copper alloys, alloy 20, copper, nickel, zirconium, titanium, tantalum, chromium, Hastelloys or generic equivalents, and combinations of these metals. The preferred metal is 316 stainless steel. An example of a nickel-copper alloy is Monet 400, which is sold generically as Alloy 400. Generic equivalents of Hastelloys are also appropriate metals. For example, generic equivalents of Hastelloy C-276 and Hastelloy C-22 include Alloy C-276 and Alloy C-22, respectively.

The distillation takes place in equipment having components with surfaces that contact sevoflurane, and the surfaces contain little or no active metal salts. The surfaces include all surfaces that come in contact with vapor or liquid phases of a crude sevoflurane product or of substantially purified sevoflurane.

In one embodiment, the equipment can be entirely made of the non-metallic and metallic materials containing little or no active metal salts. In another embodiment, only the portion of the equipment that contacts sevoflurane during distillation may be coated with the non-metallic and metallic materials containing little or no active metal salts.

Surfaces of a component may be made of a non-metallic material, and the surfaces of another component may be made of a metallic material. For example, the reboiler may be coated with 316 stainless steel, and the condenser may be made entirely of glass.

In a preferred embodiment, a non-metallic material is used as an inert coating over metallic components. For example, PFA may be used to coat the packing material used in the column.

As mentioned above, the surface of the metal components must contain little or no active metal salts that may react with sevoflurane to produce impurities. Confirmation that the surfaces of the equipment contain little or no active metal salts may be accomplished by various techniques. A preferred method is to add previously analyzed sevoflurane to the distillation system and perform a standard distillation. The distillation may, for example, be conducted using about 300 kg sevoflurane per cubic meter of equipment volume over a period of 24 hours. The resultant distillate and residual pot contents are analyzed for impurities. If there is no increase in the amount of impurities in the sevoflurane, the distillation system is confirmed to be sufficiently free of active metal salts, and is ready for use.

When metallic components are used in the distillation process equipment, constant care must be maintained in order to avoid the generation of reactive metal salts which may cause the decomposition of sevoflurane either during the distillation process or upon storage for long periods of time. Reactive metal salts are any salts which contribute to the generation of impurities in sevoflurane. Common reactive metal salts include halides, nitrates, and sulfates of the metals used. Examples of reactive metal salts include iron chloride(s), iron fluoride(s), iron nitrate(s), iron sulfate(s), copper chloride(s), copper fluoride(s), copper nitrate(s), copper sulfate(s), nickel chloride(s), nickel fluoride(s), nickel nitrate(s), and nickel sulfate(s).

The distillation system must be routinely monitored for indications of unexpected reactive metal salt formation. Monitoring techniques include periodic visual inspection of metallic components for signs of corrosion and regular monitoring of final product distillate for the presence of elevated quantities of impurities as described above.

If unacceptable quantities of reactive metal salts are detected in the distillation equipment or there is reason to believe there are salts on the surface of the equipment, the reactive metal salts must be removed and the surface of the metal components must be protected before any further processing is attempted. One potential method for accomplishing this type of purification, particularly for components made from stainless steel, is called passivation. This process involves the treatment of the surfaces of metallic equipment with an aqueous solution of a passivation agent that removes metal salts while rendering a non-inert metallic surface of the metallic equipment inert. Examples of suitable passivation agents include citric acid, nitric acid, and mixtures of nitric acid and sodium dichromate. The preferred passivation agent is nitric acid.

In a typical cleaning/recovery procedure, the equipment first is washed thoroughly with water, although this step is optional. If the pH of the discharged wash is initially less than 6, washing should be carried out until the pH of the discharged water is at least 6. The sevoflurane-contacting surfaces of the equipment are then placed in contact for a period of time with a passivation solution. After the passivation solution is removed, the equipment is rinsed repeatedly with water until all of the passivation solution and dissolved metal salts have been removed from the system. After it has been confirmed that all of the passivation solution has been removed, the equipment is dried by conventional methods.

The concentration of the passivation agent in the aqueous solution is effective at a minimum of about 1% by weight of the aqueous solution, and more preferably about 10% by weight of the aqueous solution. The maximum concentration of the passivation agent in the aqueous solution is about 90% by weight of the aqueous solution, and more preferably about 50% by weight of the aqueous solution. The contact time for the treatment of the metallic components with the aqueous solution will depend on several factors, including the concentration of the passivation agent and the amount of metal-salt contamination.

Sufficient contact time is determined retrospectively by placing the equipment back into service and monitoring the next sevoflurane distillate for the presence of unacceptably large quantities of impurities, as discussed previously. The normal time for contact of the equipment with the passivation solution is a minimum of about a quarter of an hour, and more preferably about 30 minutes. The maximum amount of time for contact of the equipment with the passivation solution is about 48 hours, preferably about 24 hours.

The contact temperature for the treatment of the metallic components with the passivation solution will depend upon several factors including the concentration of the passivation agent, and the amount of the suspected metal salt contamination. Sufficient contact temperature is determined retrospectively by placing the equipment back into service and monitoring the next sevoflurane distillate for the presence of unacceptably large quantities of impurities, as discussed previously. The contact temperature when the metallic equipment is in contact with the aqueous passivation solution is a minimum of about 20° C., more preferably a minimum of about 35° C., and more preferably about a minimum of about 50° C. The contact temperature at when the metallic equipment is in contact with the aqueous passivation solution is a maximum of about 80° C., preferably a maximum of about 70° C., and more preferably about a maximum of about 60° C. The preferred range is about 50° C. to about 60° C.

When metallic equipment used in the distillation of sevoflurane has been cleaned according to method described above, the metallic equipment may be reused to make substantially pure sevoflurane that exhibits stability at room temperature for at least two years without the addition of sevoflurane decomposition suppression agents.

In another embodiment, the invention relates to a process for obtaining commercial quantities of substantially pure sevoflurane. The process comprises:
  i) providing a crude sevoflurane product;
  ii) passivating liquid- and gas-contacting surfaces of distillation equipment capable of providing commercial quantities of sevoflurane;
  iii) distilling the crude sevoflurane product in the distillation equipment; and
  iv) recovering substantially pure sevoflurane.

The acts of providing a crude sevoflurane product, passivating liquid- and gas-contacting surfaces of distillation equipment capable of providing commercial quantities of sevoflurane, distilling the crude sevoflurane product in the distillation equipment, and storing the substantially pure sevoflurane are as described above. Preferably, sevoflurane decomposition suppression agents are not added to the sevoflurane during the distillation. The substantially pure sevoflurane may be stored up to two years in glass containers, preferably Type III glass containers, with or without the presence of sevoflurane decomposition suppression agents.

We claim:

1. A process for obtaining pharmaceutical grade, storage-stable sevoflurane comprising:
   i) providing a crude sevoflurane product;
   ii) providing distillation equipment comprising surfaces that will come into contact with sevoflurane during distillation of the crude sevoflurane product, said surfaces being selected from the group consisting of stainless steel surfaces that resist forming metal salts;
   iii) passivating said surfaces with a passivation agent consisting of nitric acid or a mixture of nitric acid and sodium dichromate to yield passivated distillation equipment;
   iv) distilling the crude sevoflurane product in the passivated distillation equipment without adding sevoflurane decomposition suppressive agents; and
   v) recovering pharmaceutical grade, storage-stable sevoflurane as a distillate as a result of said distilling.

2. The process according to claim 1, further comprising storing the pharmaceutical grade, storage-stable sevoflurane up to two years.

3. The process according to claim 2, wherein the pharmaceutical grade, storage-stable sevoflurane product is stored in glass containers.

4. The process according to claim 3, wherein the glass containers are made of Type III glass.

5. The process according to claim 3, wherein sevoflurane decomposition suppression agents are not added to sevoflurane during storage.

6. The process according to claim 1, wherein step iii) comprises:
   a) washing the stainless steel surfaces one or more times with water, and if the pH of the discharged wash is initially less than 6, continuing washing until the pH of the discharged wash is at least 6;
   b) contacting the stainless steel surfaces of the equipment that are to be treated with an aqueous solution of the passivation agent;
   c) removing the aqueous passivation agent; and
   rinsing the equipment with water, and if the pH of the discharged wash is initially less than 6, continuing washing until the pH of the discharged water is at least 6.

7. A process according to claim 1, wherein the passivation agent is nitric acid.

8. A process for removing reactive metal salts from distillation equipment comprising surfaces that will come into contact with sevoflurane during distillation of a crude sevoflurane product, said surfaces being selected from the group consisting of stainless steel surfaces that resist forming metal salts, and rendering the surfaces inert, the process comprising:
   i) washing the equipment one or more times with water, and if the pH of the discharged wash is initially less than 6, continuing washing until the pH of the discharged wash is at least 6;
   ii) contacting the surfaces of the equipment that are to be treated with an aqueous solution of a passivation agent consisting of nitric acid or a mixture of nitric acid and sodium dichromate;
   iii) removing the aqueous passivation agent; and
   iv) rinsing the equipment with water, and if the pH of the discharged wash is initially less than 6, continuing washing until the pH of the discharged water is at least 6.

9. A process according to claim 8, wherein the concentration of the passivation agent is a minimum of about 1% by weight of the aqueous passivation solution.

10. A process according to claim 8, wherein the concentration of the passivation agent is a minimum of about 10% by weight of the aqueous passivation solution.

11. A process according to claim 8, wherein the concentration of the passivation agent is a maximum of about 90% by weight of the aqueous passivation solution.

12. A process according to claim 8, wherein the concentration of the passivation agent is a maximum of about 50% by weight of the aqueous passivation solution.

13. A process according to claim 8, wherein the equipment is in contact with the aqueous passivation solution for a minimum total time period of about 0.25 hours.

14. A process according to claim 8, wherein the equipment is in contact with the aqueous passivation solution for a minimum total time period of about 0.50 hours.

15. A process according to claim 8, wherein the equipment is in contact with the aqueous passivation solution for a maximum total time period of about 48 hours.

16. A process according to claim 8, wherein the equipment is in contact with the aqueous passivation solution for a maximum total time period of about 24 hours.

17. A process according to claim 8, wherein the passivation agent is nitric acid.

18. A process according to claim 8, wherein the contact temperature when the equipment is in contact with the aqueous passivation solution is a minimum of about 20° C.

19. A process according to claim 8, wherein the contact temperature when the equipment is in contact with the aqueous passivation solution is a minimum of about 35° C.

20. A process according to claim 8, wherein the contact temperature when the equipment is in contact with the aqueous passivation solution is a minimum of about 50° C.

21. A process according to claim 8, wherein the contact temperature when the equipment is in contact with the aqueous passivation solution is a maximum of about 60° C.

22. A process according to claim 8, wherein the contact temperature when the equipment is in contact with the aqueous passivation solution is a maximum of about 70° C.

23. A process according to claim 8, wherein the contact temperature when the equipment is in contact with the aqueous passivation solution is a maximum of about 80° C.

24. The process according to claim 1, which further comprises providing the crude sevoflurane product by a process comprising reacting (a) hexafluoroisopropanol, (b) formaldehyde or a formaldehyde equivalent and (c) hydrogen fluoride.

* * * * *